(12) United States Patent
O'Brien

(10) Patent No.: US 7,198,797 B2
(45) Date of Patent: Apr. 3, 2007

(54) PROCESS FOR MAKING LARVICIDAL EVAPORATION SUPPRESSANT POWDER

(76) Inventor: Robert Neville O'Brien, 2614 Queenswood Dr., Victoria, B.C. (CA) V8N 1X5

(*) Notice: Subject to any disclaimer, the term of this patent is extended or adjusted under 35 U.S.C. 154(b) by 540 days.

(21) Appl. No.: 10/470,627

(22) Filed: Jul. 2, 2002

(65) Prior Publication Data

US 2005/0095265 A1    May 5, 2005

(51) Int. Cl.
*A01N 25/32* (2006.01)
(52) U.S. Cl. ............. 424/406; 424/405; 424/408; 424/409; 424/417; 424/421; 424/93.461; 424/93.1
(58) Field of Classification Search ............ 424/93.96, 424/93.1–93.6; 119/6.5–6.8
See application file for complete search history.

(56) References Cited

U.S. PATENT DOCUMENTS 5,567,430 A * 10/1996 Levy ................. 424/409
5,824,328 A * 10/1998 Levy ................. 424/409

* cited by examiner

*Primary Examiner*—Neil S. Levy

(57) ABSTRACT

A water-free process for converting initially non-larvicidal evaporation suppressant powder into a larvicidal variant possessing utility both for abatement of use by mosquitoes of an open water catchment as a successful breeding site, and for conserving water by suppressing the evaporation of water from the same catchment. Lauryl alcohol is used as a blending agent to facilitate even distribution of mosquito-specific entomopathogens, eg., spores of *Bacillus thuringiensis* variety *Israelensis* or *Bacillus sphaericus*, into the initially non-larvicidal evaporation suppressant powder. Cetyl alcohol and/or stearyl alcohol are the preferred monolayer-formers upon which effective evaporation suppression relies. For a variant larvicidal powder that lacks an effective evaporation suppression property, the same preferred monolayer-formers may be omitted from a blend of mosquito-specific pathogens, lauryl alcohol, and hydrated lime or, alternatively, acidified gypsum.

2 Claims, No Drawings

PROCESS FOR MAKING LARVICIDAL EVAPORATION SUPPRESSANT POWDER

BACKGROUND OF THE INVENTION

1. Technical Field

In general, this invention relates to a specially blended, powdery, larvicidal composition suitable for application to open water catchments to control local mosquito populations, and more especially to the hereinafter described water-free preparation process for making a powder that possesses utility both for abatement of use by mosquitoes of an open water catchment as a successful breeding site, and for conserving water by suppressing the evaporation of water from the same catchment.

A tried-and-proven method of abating the kind of mosquito breeding which is typically localized at a site consisting of an open water catchment is to drain the catchment or procure its drying up, thus depriving egg-laying female mosquitoes of opportunity to use that particular site for breeding. However, whenever conservation of water stored in open catchments is a high priority social objective, a "drying-the-site" method of mosquito control has to be ruled out. In realistic scenarios, therefore, there would be advantage to devising suitable means capable of simultaneously conserving water and controlling mosquitoes. The powder to be manufactured in accordance with the instant invention will constitute such means.

2. Prior Art

The field of mosquito larvicides encompasses a number of variously formulated known toxicological and non-toxicological compositions suitable for application to mosquito breeding waters. Non-toxicological compositions include those known to utilize as a larvicide at least one suitably selected organic compound capable of forming a monomolecular film, or ie., monolayer, on the water catchment surface. The film to be formed in such a case need contain no toxin which kills mosquito larvae, but instead is designed to cause them to sink and drown by so modifying the surface of a catchment that the denser-than-water larvae which normally hang suspended therefrom will be deprived of their usual means of support, viz., surface tension on a ring of hairs surrounding tracheal openings at the upwardly directed, air-snorkeling rear end of each aquatic mosquito larva.

Concerning the field of water conservation, it is wellknown that some although not all organic compounds capable of forming a monolayer on a water surface can be effective as water evaporation suppressants. Since not every kind of monolayer produces a film that is effective for practical water evaporation suppression, it would be factually insupportable to infer that, merely by the formation on mosquito breeding waters of any kind of monolayer whatsoever, that there inherently would result effective water evaporation suppression, always accompanying the intended mosquito control effect. Nor, on the other hand, would it be factually supportable to infer that every formed monolayer that does effectively suppress evaporation of water must inherently be lethal to mosquito larvae.

In 1968, the June issue of *Mosquito News* published "A FEASIBILITY STUDY ON THE UTILIZATION OF MONOMOLECULAR FILMS FOR MOSQUITO ABATEMENT", wherein Gerald A. Lorenzen and Wilmon W. Meinke reported, among other things, their finding that film-forming cetyl alcohol, ie., n-hexadecanol, which is wellknown in surface chemistry to be a compound effective for evaporation suppression use, has no larvicidal effect on the *Culex quinquefasciatus* mosquito species common in Texas.

Lorenzen and Meinke also reported that particles of cetyl alcohol floating on the water surface of test units were observed to be apparently fed upon by mosquito larvae with no ill effect to them. Plausible effect of such feeding behaviour upon the surface area coverage capacity of the amount of finely ground film-forming material used received no mention, but it may reasonably be supposed that an individual cetyl alcohol particle ingested by a mosquito larva does not subsequently participate in usual film-spreading and film-repairing processes associated with use of powdered fatty alcohols for evaporation suppression. A real prospect thus exists that presence of a high population of actively feeding mosquito larvae at a water catchment site can have a deleterious effect on certain evaporation suppression measures, specifically those wherein a fatty alcohol of high enough carbon number to be solid-phase in finely particulate bulk form is utilized. For an example of a film-spreading powder for suppressing water evaporation which contains fatty alcohol particles upon which mosquito larvae may conceivably feed, see U.S. Pat. No. 6,303,133 B1 (O'Brien), incorporated here by reference.

In 1977, the September issue of *Mosquito News* published "MOSQUITO CONTROL WITH MONOMOLECULAR ORGANIC SURFACE FILMS: I—SELECTION OF OPTIMUM FILM-FORMING AGENTS", wherein William D. Garrett and Sheldon A. White cited both the abovecited report by Lorenzen and Meinke, and A. S. Msangi's earlier research-based conclusion (1956) that n-hexadecanol produces no appreciable influence on aquatic larvae of the *Anopheles gambiae* mosquito species common in Africa.

Thus, although a monolayer of cetyl alcohol is known to suppress water evaporation effectively, deficiency of the same film-forming compound for a larvicidal role is also known.

One traceable trend respecting delineation of criteria for optimum materials selection directed to forming monolayers capable of interfering with mosquito breeding diverges in major respects from another traceable trend respecting delineation of criteria for optimum materials selection directed to forming monolayers that effectively suppress evaporation.

Preference for a liquid state for film-forming material in its pre-distribution bulk phase, and for a high fluidity of the formed monolayer on water are two of the several key criteria listed by Garrett and White in the second of the abovecited *Mosquito News* reports, which from a physicochemical standpoint are criteria conducive to larvicidal effectiveness. The same two criteria, unfortunately, tend to be incompatible with effective suppression of water evaporation from an open reservoir, particularly if the film-forming material selected is a normally solid-phase fatty alcohol.

According to a classic surface chemistry textbook, *INSOLUBLE MONOLAYERS AT LIQUID-GAS INTERFACES* by George L. Gaines, Jr. (Interscience Publishers, 1966), high fluidity as a formed monolayer property runs counter to optimum effectiveness at suppressing evaporation. The kind of monolayer that imposes higher resistance (than other kinds) to egress through it of water vapor is the so-called "condensed film" kind of monolayer, featuring close side-by-side packing of upright unbranched molecular chains. Extent of vapor passage resistance increases with chain length, provided the chain is truly linear so that adjacent molecules in a film can be closely packed.

Fatty alcohols with a carbon number lower than 14 are liquid at standard temperature, and even if unbranched form a film of high fluidity on water, rather than forming the condensed kind of monomolecular film that retards evaporation significantly more effectively. Thus, lauryl alcohol, ie., dodecanol, with 12 carbon atoms per molecule, would not be recommended for optimization of evaporation suppression properties, although it would be selectable for its ability to cause mosquito larvae mortality in the manner reported by Lorenzen and Meinke in the first of the abovecited *Mosquito News* reports.

The discussions of larvicidal agencies present in both abovecited *Mosquito News* reports are predicated on the concept that mosquito breeding at a given open water site can feasibly be abated on a non-toxicological basis by suitably modifying the water surface to prevent normal larval respiration.

Another relevant factor in the background of the instant invention is the known use of biological mosquito larvicides comprising toxin-carrying spores of microbial species, eg., *Bacillus thuringiensis* variety Israelensis, and *Bacillus sphaericus*, which shall collectively be referred to hereinafter as 'mosquito-specific entomopathogens'. The toxins are specifically lethal to larvae of mosquitoes when the minute *Bacillus* spores are ingested thereby.

It has also been suggested that a so-called "synergistic" mode of treatment of a mosquito breeding site can be practiced, wherein larvicidal agencies include both the surface tension reduction by a monolayer that drowns mosquito larvae, and the use of mosquito-specific entomopathogens to poison them. Film-forming compounds recommended for known compositions for carrying out such a "drowning-plus-poisoning" type of larvicidal treatment are compatible with the optimized materials selection criteria proposed in the abovecited Garrett and White *Mosquito News* report, because these are typically branched chain compounds that procure the highly fluid—rather than condensed—kind of monolayer. For a citable example wherein ethoxylated and branched-chain compounds are recommended see the "Insecticide composition for controlling insects which have an aquatic breeding site" by A. I. McMullen, U.S. Pat. No. 4,707,359 (Nov. 17, 1987). The composition by McMullen is not designed to procure effective evaporation suppression.

Significantly, concerning preparation of formulations according to the McMullen insecticidal monolayer-forming invention, problems that would be encountered if attempting to evenly distribute mosquito-specific entomopathogens within a main body comprising film-forming constituents were easily avoided by the use of water as a dispersion medium during product preparation. Contrastingly, the film-spreading powder of abovecited U.S. Pat. No. 6,303,133 B1 (O'Brien) does not lend itself during its preparation process to admixture of its constituents with water, because addition of water during processing would prematurely activate ionization of the slaked lime, ie., calcium hydroxide, that is included to provide a unique dispersal mechanism that takes effect when the powder is broadcast upon a body of water intended to be coated by an effective evaporation-suppressing monolayer. Without feasibility of using water in the processing, a real problem of how to evenly distribute mosquito-specific entomopathogens within a main body comprising dry particulate film-forming and other constituents arises.

It has already been noted above that the O'Brien patented powder, so long as it places finely divided alcohol particles on a water catchment surface, is susceptible to a number of such particles being ingested by mosquito larvae, if present, thus suffering a loss of reserve film-forming material that would be expected to be of a magnitude proportionate to the number of feeding larvae. Insofar as is known at this time of disclosing the instant invention, nobody has previously suggested the specific manner of resolving this problem that is presently proposed.

As a final point closing background discussion, it is acknowledged as having already been known in the general art pertaining to insecticides to disperse mosquito-specific entomopathogens in a quantity of liquid-phase lauryl alcohol, ie., dodecanol, which is not a satisfactory evaporation suppressant material, although as far back as 1968 (Lorenzen and Meinke) this 12-carbon fatty alcohol was proposed to be suitable for forming a monomolecular film intended specifically for mosquito abatement use.

BRIEF SUMMARY OF THE INVENTION

One important technical object of the invention is to devise a way to reduce the susceptibility of finely divided fatty alcohol particles to being ingested by mosquito larvae, when such particles are located on the surface of a water catchment infested by the larvae.

Another important technical object of the invention is to devise a water-free mode of processing that distributes particulate mosquito-specific entomopathogens evenly within a quantity of film-spreading powder containing, together with other chemical constituents, finely particulate fatty alcohol, preferably cetyl alcohol, stearyl alcohol, or a blend of these two compounds.

The overarching object of the invention is procurement of a special powder that possesses utility both for abatement of use by mosquitoes of an open water catchment as a successful breeding site, and for conserving water by suppressing the evaporation of water from the same catchment.

It has been found that the foregoing objects can substantially be satisfied by making a larvicidal variant of a known hydrated lime-containing "film-spreading powder for suppressing water evaporation" that has previously been described in U.S. Pat. No. 6,303,133 B1 (O'Brien). This variant of that hydrated lime-containing powder is rendered larvicidal by virtue of stirring or otherwise intimately blending a suitable proportion of known mosquito-specific entomopathogens, dispersed in lauryl alcohol, into constituents of the original composition made in accordance with the cited O'Brien patent.

It has been found that the foregoing objects can also substantially be satisfied by making a larvicidal variant of an acidified gypsum-containing "composition for reducing evaporation at sites both on land and open water" that is disclosed in U.S. patent application Ser. No. 09/739,895 (O'Brien). Equivalently as with the hydrated lime-containing variant, this acidified gypsum-containing variant is rendered larvicidal by virtue of stirring or otherwise intimately blending a suitable proportion of known mosquito-specific entomopathogens, dispersed in lauryl alcohol, into constituents of the original composition made in accordance with the cited O'Brien patent application.

Due to pre-dispersal of mosquito-specific entomopathogens in lauryl alcohol before blending with other constituents, it is surprisingly easy to evenly distribute the entomopathogens throughout the volume of a powdered evaporation suppressing composition, without the use of water in the process.

The resulting product is storable for considerable periods of time in sacks, drums, etc., that can be handled and shipped without a deleterious internal settling and gravitational separation of constituents that would likely occur if the lauryl alcohol were not used and instead only the dry entomopathogenic material, eg. *Bacillus thuringiensis* spores, were directly combined with the original dry particulate evaporation suppressant materials.

When the resulting product is broadcast upon the surface of an open water catchment, for example by a crop-dusting type mode of distribution from an aircraft overflying a reservoir, all the highly desirable effects associated with the unique ionization-caused particle repulsion achieved in accordance with the disclosures of the abovecited O'Brien patent and patent application are retained. The film-spreading and film-repairing processes are the same as for the corresponding composition versions without larvicidal constituents.

A significant limitation to be observed when making the powder of the instant invention is to keep the lauryl alcohol content at a minimal level commensurate to effectively distributing the *Bacillus thuringiensis* spores or equivalent entomopathogenic particulate material with the other normally solid-phase composition constituents. Even though lauryl alcohol is itself normally liquid-phase at standard temperature, when absorbed by sufficient powder of the balance of other constituents it ceases to occur in the end-product as a macroscopic-scale liquid. It is no intention associated with the instant invention to make an oily "sludge" or "slurry" instead of the intentionally devised dry powder, but such an oily and non-particulated result would of course be expected if too high a proportion of lauryl alcohol were used.

Additional details relating to carrying out the invention follow, starting with review of precursor O'Brien evaporation suppressant powders.

DETAILED DESCRIPTION OF THE INVENTION

Considered a parent disclosure, U.S. Pat. No. 6,303,133 B1 taught a powdery hydrated lime-containing evaporation suppressant having particles that repel one another during a water-induced ionization process. Prior art had not taught combination of long-chain solid-phase fatty alcohols with hydrated lime, ie., calcium hydroxide. The composition of the parent disclosure comprises microparticles of long-chain fatty alcohol and calcium hydroxide, and has been shown upon water induced ionization to enhance film-spreading on a water surface due to the phenomenon of the particles mutually repelling one another in a manner not apparent in prior art. As already indicated in the BRIEF DESCRIPTION section above, the instant invention, by further including a component consisting of mosquito-specific entomopathogens dispersed in lauryl alcohol, contributes a new and previously unsuggested way to reduce the number of solid-phase fatty alcohol particles possibly ingested by mosquito larvae infesting a body of water, while retaining the earlier disclosed phenomenon of mutual particles' repulsion.

Considered and filed as a continuation-in-part of the aforesaid lime-containing composition's disclosure, U.S. patent application Ser. No. 09/739,895 which is here incorporated by reference substituted—in place of the lime of the parent invention—an "acidified gypsum" component consisting of about 5 milliliters of sulfuric acid per 300 grams of crushed gypsum. Blending unemulsified detergent range fatty alcohols such as cetyl alcohol and/or stearyl alcohol with the acidified gypsum produces an effective evaporation suppressant which works on open bodies of water in the same manner as the limy parent. As indicated in the BRIEF DESCRIPTION section above, the instant invention, by further including a composition component consisting of known mosquito-specific entomopathogens dispersed in lauryl alcohol, promotes reduction of the number of solid-phase fatty alcohol particles likely ingested by mosquito larvae, while retaining—in the same manner for the acidified gypsum-containing evaporation suppressant as with hydrated lime-containing powder for evaporation suppression—the earlier disclosed phenomenon of mutual particles' repulsion. A fact undisclosed before now is that an equivalent component to the "acidified gypsum" can be made using—in substitution for sulfuric acid—oxalic acid or other di-functional acid with similar magnitude respecting ionization constant.

The explanation of spreading enhancement for the self-propelling precursor powder formulations of O'Brien is that "fast" ions ionized on contact of the powder with water leave a net positive charge on particles in the case of lime blended with fatty alcohol, and a net negative charge in the case of acidified gypsum similarly blended. Outdoor pool tests have shown the spreading of of such precursor powders across a water surface to reach about 10 kmh., which is much faster than alcohol films spread from fatty alcohol solid-phase particles unblended with ionizable crushed minerals and thus absent the recently discovered and exploited particles repulsion effect.

It is now apparent that enough power is developed to aquatically propel other materials blended into a powder, besides the insoluble fatty alcohol component and the dwindling partly soluble mineral component that "fuels" the propulsion. A variety of additional types of components appears feasible, including fertilizers, fish food, aquatic herbicides, and toxins that are insecticidal by mechanisms other than the biological type involved with use of mosquito-specific entomopathogens. In every case, however, the added substance must be pre-tested for inertness with regard to chemical reaction with the insoluble monolayer former and whichever ionizable crushed mineral component is used, inertness being needed during both the preparation process and when applied in the field for the end-use.

A composition that meets the main object of providing both water conservation by suppressing evaporation and mosquito control by larvicidal effect is readily manufacturable by a process that basically adds—to the disclosed steps for making the patented precursor evaporation suppressant formulations of O'Brien—a further step for blending in a suitable amount of mosquito-specific entomopathogens pre-dispersed in lauryl alcohol. This step should not be incorporated at the melt-processing stage of making either of the precursor evaporation suppressant powders, for two reasons: the heat involved would kill the microbial entomopathogens; and undesired loss by volatilization of some of the lauryl alcohol would occur. With options next to be described regarding the further blending step, the proportion of larvicidal component relative to evaporation suppressing component can be adjusted higher or lower depending on extent of mosquito larvae infestation and/or need for a predeterminable amount of evaporation suppression coverage.

One blending option is to absorb into a quantity of one of the precursor evaporation suppressant powders a quantity of pre-mixed dispersion of mosquito-specific entomopathogens in lauryl alcohol. Such a larvicidal dispersion is known to be sprayable as a liquid provided excessive content of entomopathogen spores is avoided so as to preserve a sprayable consistency. In this case the larvicidal component can be incorporated into the precursor powder by spraying the former onto the latter in a proportion within ability of the powder to sufficiently absorb lauryl alcohol so that in the finished product composition it retains no macroscopically liquid character, even though at a temperature above its freezing point. This option lends itself to high volume continuous production of a ready-to-use composition having well balanced properties both for water conservation and mosquito control, and which is especially suitable for marketing to large-scale users expected to treat large public water storage reservoirs.

The alternative blending option lends itself better to batch-type processing and entails making two powders that may be stockpiled separately until an appropriate need-circumstance is identified that calls for their being blended. Adjustments of the balance between evaporation suppression coverage, on the one hand, and number of mosquito larvae per hectare of water surface anticipated to be killed by ingestion of entomopathogens put amidst them, on the other hand, are in this case left to the product user to make, depending on local circumstances. For clarity, the property of effectively suppressing evaporation of water is possessed exclusively by one of the two powders, and the larvicidal property is possessed exclusively by the other.

A particular pond or rice paddy may for a limited time require some, but comparatively little, use of evaporation suppressant material, and may be more in need of a mosquito larvicide due to being heavily infested. There may be occassion in connection with particular rice cropping practices to allow a paddy to dry out on a definite schedule. Timed reduction of—and ultimate elimination of—use of evaporation suppressant would allow this; but the larvicidal property of the other powder may remain needed until a later date than that at which use of evaporation suppressant should cease. Thus it is logical to have the two blendable powders kept separately for blending as, when, and if desired, thereby accomodating a greater range of use-exigencies.

It is expected that the relative amount of lauryl alcohol fully absorbable by crushed mineral particles of hydrated lime or acidified gypsum will be somewhat greater when the mineral components have not been previously intimately pre-combined with cetyl alcohol and/or stearyl alcohol in a melt thereof. This means that a highly effective larvicidal powder lacking in evaporation suppression effectiveness is manufacturable by combining the mosquito-specific pathogens, lauryl alcohol, and crushed mineral components, sans presence of cetyl alcohol and/or stearyl alcohol. Such a powder has been developed in order to facilitate end-property adjustments in a preferred composition made by the optional process of blending the two powders as here suggested, viz., the one exclusively possessing the larvicidal property; the other exclusively procuring effective evaporation suppression. To here disclose the two blendable powders that can go into a final product capable of use simultaneously for both mosquito control and water conservation, but easily adjustable with respect to relative extent of effectiveness towards those two purposes, cannot help but incidentally also disclose the one of the two blendable powders that is larvicidal only, and may even be used alone in those cases where evaporation suppression is not required.

Most generally however, in contemplation especially of large-scale continuous production in accordance with the first option for enacting the basic process of the instant invention, it is easy to provide a ready-to-use powder that without requiring tailored blending of two powders by end users will achieve good balance between good evaporation suppression effectiveness and larvicidal effectiveness without tilting extremely one way or the other, merely by adding lauryl alcohol plus mosquito-specific entomopathogens to a main body of powder initially comprising one or the other of the precursor evaporation suppressant powders by O'Brien.

Assuming propriety of incorporating by reference the disclosed content of the abovecited O'Brien patent and patent application, it should be apparent at this point that competent workers in the art, after studying all the foregoing new subject-matter of the present disclosure, will be armed to carry out the instant invention with no more than routine experimentation needed and/or desired as may be appropriate to end-use circumstances.

What I claim is:

1. A method of controlling aquatic environment insects by
    a) making a rapidly spreading initially non-larvicidal, evaporation suppressant powder by blending unbranched fatty alcohols selected from the group consisting of stearyl alcohol, cetyl alcohol and mixtures thereof,
    in a suitable proportion with a mineral component selected from the group consisting of hydrated lime, acidified gypsum and bicarbonate of soda:
    b) coating a mosquito specific entomopathogen with a mixture of lauryl alcohol and a mineral oil, the mineral oil at being less that 10% of the lauryl alcohol, to provide a hydrophobic larvicide,
    c) while providing temperature low enough not to damage larvicide potency
    d) converting the non-larvicidal evaporation suppressant powder into a larvicidal evaporation suppress and powder effective to control a target pest, by intimately blending said initially non-larvicidal evaporation suppressant powder together with said larvicidal mixture, in sufficient proportions to provide a lethal dose of larvicidal and rapid spread of evaporation suppression film, and
    e) spreading the resultant powder on water harboring or known to harbor target insect larvae, such that sufficient effective larvicide will be rapidly spread to all parts of the target water surface, and the film former will suppress the evaporation of water.

2. The method of claim 1, wherein the larvicide is: Bti (*Bacillus Thuringiensis Israelensis*).

* * * * *